US009390230B2

(12) United States Patent
Kim et al.

(10) Patent No.: US 9,390,230 B2
(45) Date of Patent: Jul. 12, 2016

(54) RADIATION TREATMENT PLANNING APPARATUS AND METHOD THEREOF

(71) Applicant: Infinitt Healthcare Co., Ltd., Guro-dong, Guro-gu (KR)

(72) Inventors: Jin Jun Kim, Seoul (KR); Moo Hyun Park, Seoul (KR); Tae Hun An, Seoul (KR)

(73) Assignee: Infinitt Healthcare Co., Ltd., Seoul (KR)

( * ) Notice: Subject to any disclaimer, the term of this patent is extended or adjusted under 35 U.S.C. 154(b) by 0 days.

(21) Appl. No.: 13/936,649

(22) Filed: Jul. 8, 2013

(65) Prior Publication Data

US 2014/0019440 A1 Jan. 16, 2014

(30) Foreign Application Priority Data

Jul. 12, 2012 (KR) .................. 10-2012-0075824

(51) Int. Cl.
G06F 19/00 (2011.01)
A61N 5/10 (2006.01)
(52) U.S. Cl.
CPC .............. *G06F 19/34* (2013.01); *A61N 5/1038* (2013.01); *G06F 19/3481* (2013.01); *G06F 19/321* (2013.01)
(58) Field of Classification Search
None
See application file for complete search history.

(56) References Cited

U.S. PATENT DOCUMENTS 6,754,374 B1 * 6/2004 Miller et al. ................. 382/128
7,362,848 B2 4/2008 Saracen et al.
7,593,505 B2 9/2009 Saracen et al.
7,995,813 B2 8/2011 Foshee et al.
8,121,252 B2 2/2012 Nord et al.
8,666,128 B2 * 3/2014 Chaney et al. ................ 382/128
8,774,358 B2 * 7/2014 Zankowski ..................... 378/65
2007/0041496 A1 2/2007 Olivera et al.

(Continued)

FOREIGN PATENT DOCUMENTS

JP  11-206895 A   8/1999
JP  2006167117 A  6/2006

(Continued)

OTHER PUBLICATIONS

P Bhatnagar, M Subesinghe, C Patel, R Prestwich, and AF Scarsbrook, "Functional Imaging for Radiation Treatment Planning, Response Assessment, and Adaptive Therapy in Head and Neck Cancer," Radiographics. 33(7):1909-29, published 2013, presented as an education exhibit at the 2011 RSNA Annual Meeting.*

(Continued)

*Primary Examiner* — Matthew Bella
*Assistant Examiner* — Soo Shin
(74) *Attorney, Agent, or Firm* — Mintz Levin Cohn Ferris Glovsky and Popeo, P.C.; Kongsik Kim; Jonathan P. Western

(57) ABSTRACT

A radiation treatment planning apparatus and method thereof are disclosed. The radiation treatment planning apparatus according to an embodiment of the present invention includes a processor configured to acquire first radiation therapy plan (RTP) data based on a medical image of a region of interest of a patient; acquire radiation therapy results data for the region of interest based on the first RTP data; and generate third RTP data from second RTP data preset for the region of interest using the radiation therapy results data.

8 Claims, 8 Drawing Sheets

(56) References Cited

U.S. PATENT DOCUMENTS

| | | | |
|---|---|---|---|
| 2007/0041498 A1 | 2/2007 | Olivera et al. | |
| 2007/0104316 A1 | 5/2007 | Ruchala et al. | |
| 2008/0275309 A1 | 11/2008 | Stivoric et al. | |
| 2009/0226060 A1* | 9/2009 | Gering et al. | 382/128 |
| 2011/0267343 A1 | 11/2011 | Foshee et al. | |
| 2012/0123184 A1* | 5/2012 | Otto | A61N 5/1067 600/1 |
| 2013/0085343 A1* | 4/2013 | Toimela et al. | 600/300 |
| 2013/0191146 A1* | 7/2013 | Park et al. | 705/2 |
| 2013/0230224 A1* | 9/2013 | Claude et al. | 382/131 |
| 2013/0274537 A1 | 10/2013 | Park | |

FOREIGN PATENT DOCUMENTS

| | | |
|---|---|---|
| KR | 10-2009-0119522 | 11/2009 |
| KR | 10-2010-0119103 A | 11/2010 |
| KR | 10-2010-0119106 | 11/2010 |
| KR | 101090386 B1 | 11/2011 |
| KR | 10-2012-0076672 | 7/2012 |

OTHER PUBLICATIONS

Bhatnagar, P, Subesinghe, M, Prestwich, R, Gilbert, A, Sen, M, Scarsbrook, A, Functional Imaging for Treatment Planning, Response Assessment, and Adaptive Therapy in Head and Neck Cancer. Radiological Society of North America 2011 Scientific Assembly and Annual Meeting, Nov. 26-Dec. 2, 2011 ,Chicago IL. http://archive.rsna.org/2011/110132.*

Birkby S and Harmon SP, "Reviewing RSNA Education Exhibits for RadioGraphics: The Keystone to Journal Success," RadioGraphics vol. 22, No. 4, 2002. pp. 907-909.*

L. Xing, J. Siebers, and P. Keall, "Computational Challenges for Image-Guided Radiation Therapy: Framework and Current Research," Seminars in Radiation Oncology, Oct. 2007, vol. 17, Issue 4, pp: 245-257.*

* cited by examiner

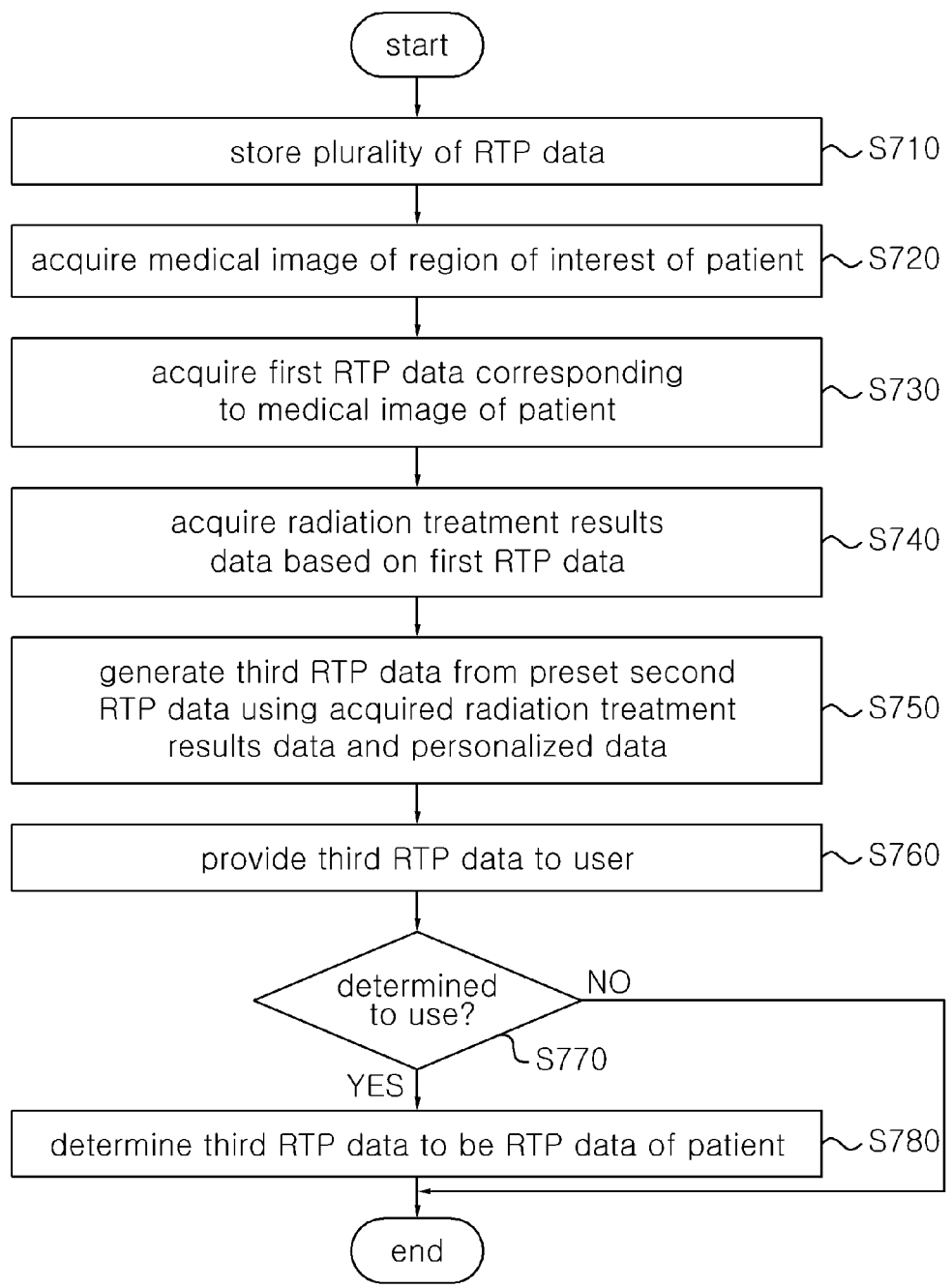

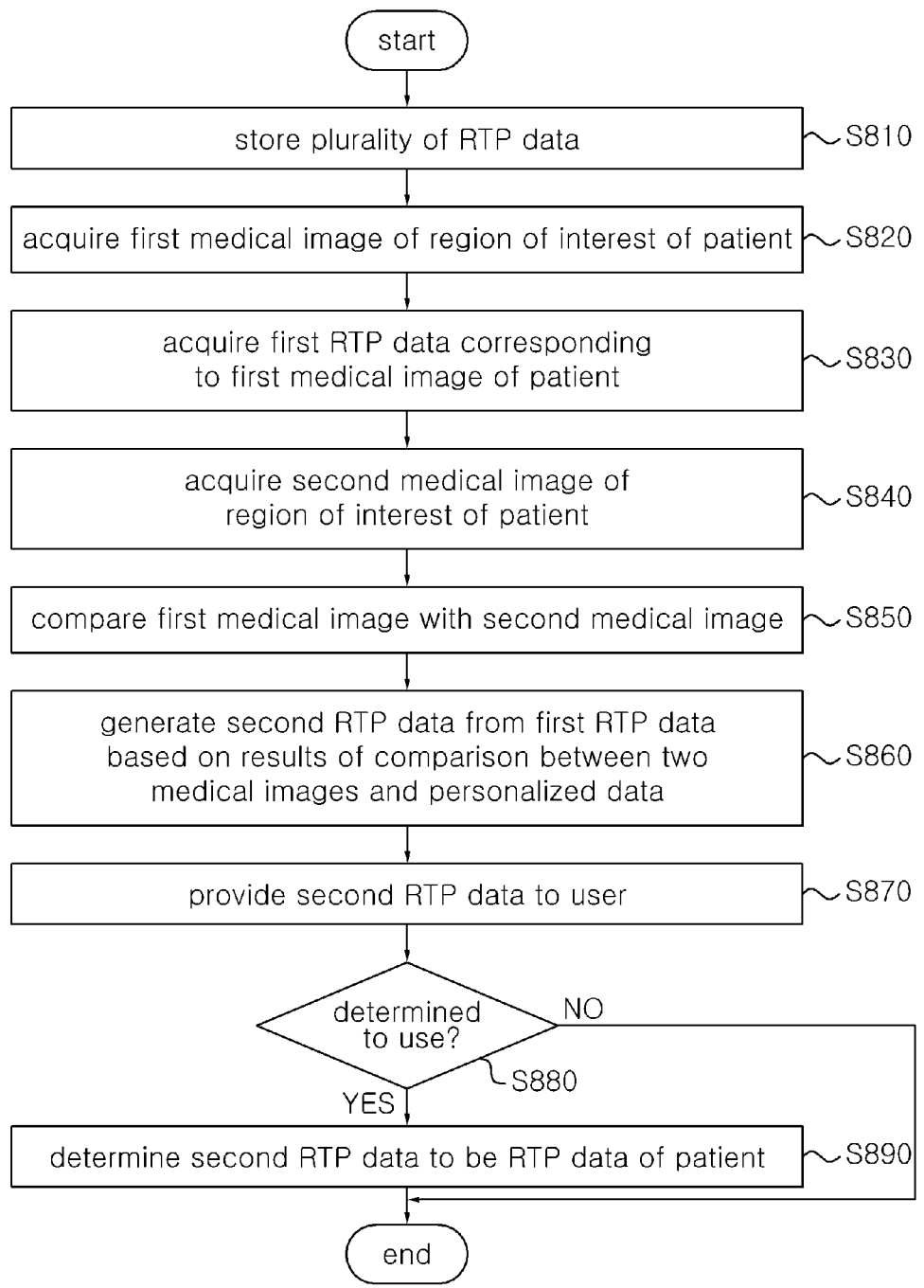

ations and patients'medical examination dand accordingly treat# RADIATION TREATMENT PLANNING APPARATUS AND METHOD THEREOF

CROSS-REFERENCE TO RELATED APPLICATION

This application claims under 35 U.S.C. §119(a) the benefit of Korean Application No. 10-2012-0075824 filed on Jul. 12, 2012, which is incorporated herein by reference.

TECHNICAL FIELD

The present invention relates to RTP (radiation treatment planning or radiation therapy plan) and, more particularly, to an RTP apparatus and method that are capable of establishing a new radiation treatment plan or radiation therapy plan (RTP) using past RTP data and radiation treatment results (or radiation therapy results) upon establishing a subsequent RTP.

BACKGROUND ART

Generally, in hospitals, many systems or apparatuses should be used to perform radiation treatment. These systems and apparatuses include an electronic medical record (EMR) system, an order communication system (OCS), a picture archiving and communication system (PACS), an RTP system, and a radiation treatment apparatus (for example, a linear accelerator (LINAC)).

The OCS is a system that transfers a database (DB) in which a variety of types of medical information and patients' medical examination data are stored and prescriptions which are written when doctors examine patients to individual corresponding treatment departments over a communication network.

The EMR system is a system that is configured for the purposes of the storage and searching of electronic medical records.

The PACS is a system that can store images captured by at least one of medical imaging devices, including a Computed Tomography (CT) scanner, a Magnetic Resonance Imaging (MRI) scanner, a Positron Emission Tomography (PET) scanner, a CT simulator, and a Computed Radiography (CR) system, in the form of computer files and transfer them, and is equipment that has been introduced into most middle-scale hospitals.

The RTP system is a system for establishing (drawing up) a radiation treatment plan for a patient using a program, and is configured to establish a radiation treatment plan, that is, it draws up radiation treatment plan information and calculates and reviews radiation doses. Using such an RTP system, a user may select an optimal image from among images of a cancer region of a patient acquired by a CT scanner or an MRI scanner, or may view a medical image of the patient, directly convert the image into a digital image, perform basic image processing on the digital image, set reference coordinates for the acquired image, perform contouring on each region, and calculate the direction and dose of a radiation beam based on the size of cancer tissue.

The fundamental principle of radiation treatment is intended to minimize not only acute and chronic radioactive reactions or complications, which may occur in normal tissue, but also the occurrence of a secondary tumor while increasing the effects of cancer treatment. For this purpose, there is a need to establish an appropriate radiation treatment plan.

The radiation treatment apparatus is an apparatus that actually performs radiation treatment on a patient according to an RTP that is drawn up by the RTP system.

The tumor treatment methods of radiation oncology have been newly developed and diversified, and accordingly treatment apparatuses and applications for the various treatment methods have been newly developed.

In the field of radiation oncology, the process of radiation treatment that is performed on a patient is as follows. First, in order to acquire information about the tumor of a patient, medical images of the patient are acquired via a medical imaging device. Thereafter, an RTP is made based on the medical images of the patient via an RTP system. Thereafter, radiation treatment is performed using a radiation treatment apparatus based on the RTP that has been made via the RTP system.

In this case, a LINAC, a Brachytherapy system, a Cyberknife, and a tomotherapy system have been developed and used as radiation treatment apparatuses, and these radiation treatment apparatuses are appropriately selected and used depending on the state of the tumor of a patient and the region of treatment.

An RTP system according to the technology of a conventional embodiment establishes radiation treatment plans (RTPs) using only medical images of patients. That is, since the conventional RTP system does not take into account the states and ages of patients, the same RTP may be established and then radiation treatment may be performed based on the same RTP, even in the case in which the ages of patients are different or the patients have singularities.

Accordingly, there arises a need for an apparatus for establishing RTPs using information about the characteristics of patients as well as medical images.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made keeping in mind the above problems occurring in the prior art, and an object of the present invention is to provide an RTP apparatus and method that generates new RTP data using radiation treatment results data based on the previous RTP data of a patient and the personalized data of the patient, thereby reducing the time and the cost that are required to establish an RTP.

Another object of the present invention is to provide an RTP apparatus and method that can generate new RTP data in accordance with radiation treatment results based on a past RTP and the purpose of radiation treatment.

A further object of the present invention is to provide an RTP apparatus and method that generates RTP data using a medical image of a patient acquired before the generation of RTP data, a medical image acquired after the generation of the RTP data, and the personalized data of the patient.

In order to accomplish the above objects, according to an embodiment of the present invention, there is provided an RTP apparatus, including a treatment plan acquisition unit configured to acquire first RTP data based on a medical image of a region of interest of a patient; a treatment results acquisition unit configured to acquire radiation treatment results data for the region of interest based on the first RTP data; and a treatment plan generation unit configured to generate third RTP data from second RTP data preset for the region of interest using the radiation treatment results data.

The treatment plan generation unit may generate the third RTP data from the second RTP data using the radiation treatment results data and personalized data of the patient. The personalized data may include at least one of age, gender, weight, height, medical history, occurrence of menopause, diagnosis, an Eastern Cooperative Oncology Group (ECOG)/Karnofsky Performance Status (KPS) index, occurrence of metastasis, a primary Tumor, regional lymph Node, distant Metastasis (TNM) class, chemical therapy, a region of treatment, a treatment pattern, immunity, sensitivity, and singularity of past treatment.

The treatment plan generation unit may generate the third RTP data from the second RTP data using the radiation treatment results data and the predetermined purpose of treatment of the second RTP data.

The treatment plan acquisition unit may acquire the first RTP data from among a plurality of preset RTP data based on at least one of the medical image and the personalized data of the patient.

The second RTP data may be the first RTP data; and the treatment plan generation unit may generate the third RTP data from the first RTP data using the first RTP data and the radiation treatment results data.

The RTP apparatus may further include a determination unit configured to provide the generated third RTP data to a user, and to determine whether to use the third RTP data as RTP data of the patient in accordance with input of the user.

According to another embodiment of the present invention, there is provided an RTP apparatus, including a treatment plan acquisition unit configured to acquire first RTP data based on a first medical image of a region of interest of a patient; a medical image comparison unit configured to compare a second medical image acquired for the region of interest with the first medical image; and a treatment plan generation unit configured to generate second RTP data from the first RTP data based on results of the comparison between the first medical image and the second medical image.

The treatment plan generation unit may generate the second RTP data from the first RTP data using the results of the comparison between the first medical image and second medical image and personalized data of the patient.

According to an embodiment of the present invention, there is provided an RTP system, including a treatment plan acquisition unit configured to acquire first RTP data based on a medical image of a region of interest of a patient; a data acquisition unit configured to request and receive radiation treatment results data for the region of interest of the patient based on the first RTP data and personalized data of the patient from a preset server; and a treatment plan generation unit configured to generate third RTP data from second RTP data preset for the region of interest using the acquired radiation treatment results data and the personalized data of the patient.

According to an embodiment of the present invention, there is provided an RTP method, including acquiring, by a processor, first RTP data based on a medical image of a region of interest of a patient; acquiring, by a processor, radiation treatment results data for the region of interest based on the first RTP data; and generating, by a processor, third RTP data from second RTP data preset for the region of interest using the radiation treatment results data.

According to another embodiment of the present invention, there is provided an RTP method, including acquiring, by a processor, first RTP data based on a first medical image of a region of interest of a patient; acquiring, by a processor, a second medical image of the region of interest; comparing, by a processor, the second medical image with the first medical image; and generating, by a processor, second RTP data from the first RTP data based on results of the comparison between the first and second medical images.

BRIEF DESCRIPTION OF THE DRAWINGS

FIG. 7 shows an operation flowchart of an RTP method according to an embodiment of the present invention; and FIG. 8 shows an operation flowchart of an RTP method according to another embodiment of the present invention.

DETAILED DESCRIPTION OF THE DISCLOSURE

The above and other objects and features of the present invention will be more clearly understood from the following detailed description taken with reference to the accompanying drawings.

The terms used herein are used merely to describe specific embodiments, but are not intended to limit the present invention. The singular expressions include plural expressions unless explicitly stated otherwise in the context thereof. It should be appreciated that in this application, the terms "include(s)," "comprise(s)", "including" and "comprising" are intended to denote the presence of the characteristics, numbers, steps, operations, elements, or components described herein, or combinations thereof, but do not exclude the probability of presence or addition of one or more other characteristics, numbers, steps, operations, elements, components, or combinations thereof.

Unless defined otherwise, all terms used herein, including technical terms or scientific terms, have the same meanings as those generally understood by persons of ordinary skill in the technical field to which the present invention pertains. The terms, such as terms that are generally used and defined in dictionaries, should be construed as having meanings identical to those that are used in the context of related technology, and should not be construed as having ideal or excessively formal meanings unless explicitly defined otherwise.

Preferred embodiments of the present invention will be described in detail with reference to the accompanying drawings. In the following description of the present invention, if it is determined that detailed descriptions of related well-known configurations or functions may make the gist of the present invention obvious, the detailed descriptions will be omitted.

However, the present invention is not restricted or limited to the embodiments. The same reference symbols represented throughout the drawings designate the same elements.

A radiation treatment planning (RTP) apparatus and method according to embodiments of the present invention will be described in detail below with reference to FIGS. 1 to 8.

Figure 1:
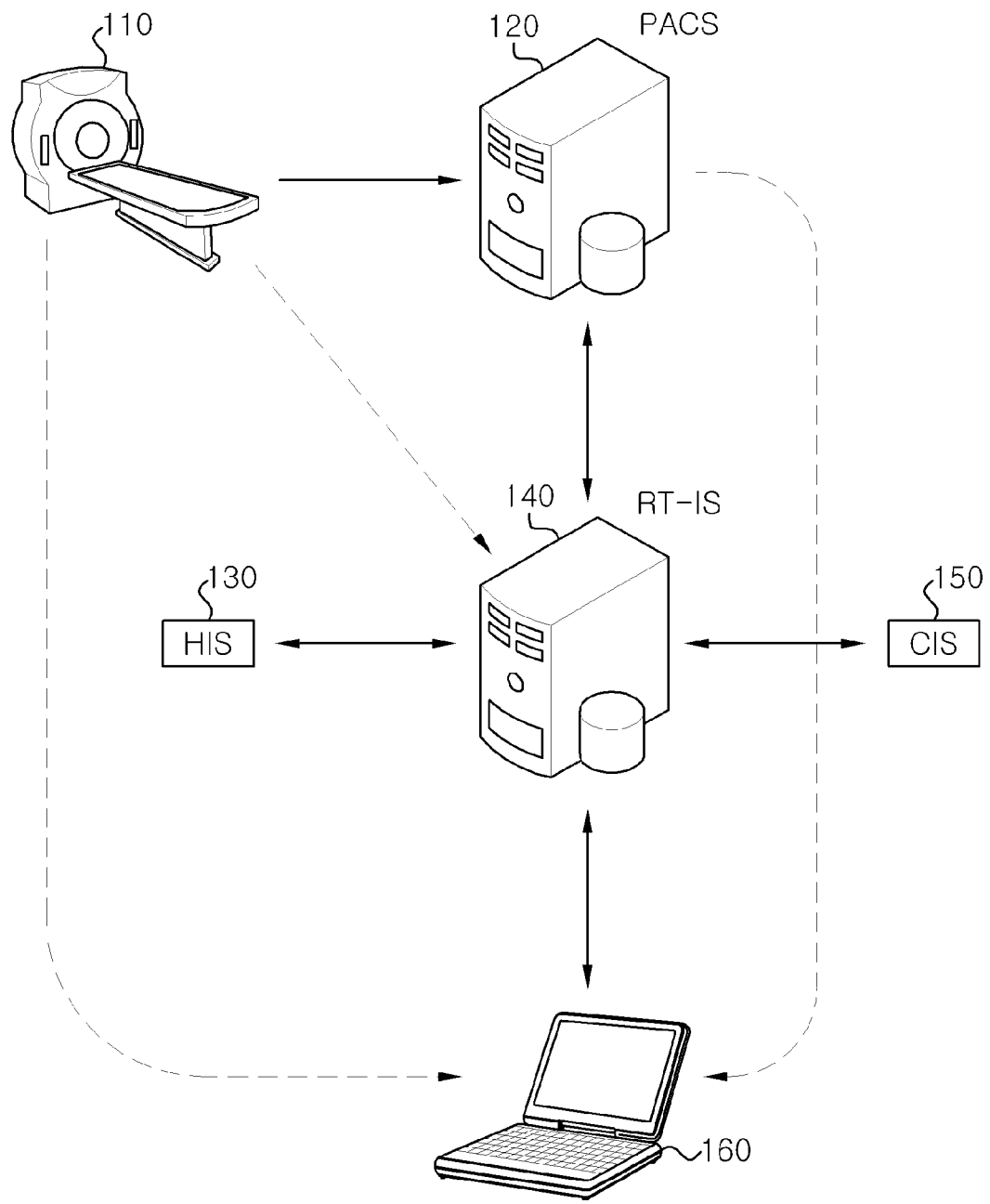
FIG. 1 shows a system of an embodiment illustrating an RTP apparatus according to the present invention.

FIG. 1 shows a system of an embodiment illustrating an RTP apparatus according to the present invention.

Referring to FIG. 1, the system includes a medical imaging device 110, a picture archiving and communication system (PACS) 120, a hospital information system (HIS) 130, a radiation treatment information management server (RT-IS) 140, a clinical information system (CIS) 150, and a client device 160.

The medical imaging device 110 is a device for acquiring medical images of a patient, and is configured to capture medical images of the patient, to convert the captured medical images into a Digital Imaging and Communications in Medicine (DICOM) format or a non-DICOM format, and to transfer resulting medical images to at least one of the PACS 120, the RT-IS 140, and the client device 160.

In this case, the medical imaging device 110 may include a Computed Tomography (CT) scanner, a Magnetic Resonance Imaging (MRI) scanner, a Positron Emission Tomography (PET) scanner, a CT simulator, and a Computed Radiography (CR) system.

The PACS 120 stores the medical images received from the medical imaging device 110 in a DICOM format, and transfers the stored medical images to a device or a system which requests the medical images.

In this case, the PACS 120 may transfer the medical images to at least one of the RT-IS 140 and the client device 160.

The HIS 130 is a system for computerizing and automating the overall management tasks of a hospital, and is configured to manage and transfer all data occurring within the hospital in connection with the registration of patients to medical treatment and accounting, and efficiently manage all administration tasks of the hospital.

In this case, the HIS 130 may manage and transfer data in conjunction with an OCS, an EMR system, etc.

The CIS 150 is a digital clinical system for aiding in storing biometric signals and data generated from electrocardiogram (ECG) equipment and typical clinical equipment in a digital format and aiding in enabling the signals and data to be retrieved and examined over a network.

The RT-IS 140 is a server for storing and managing radiation treatment (RT)-related information, and is configured to store medical images of a patient, previous RTP data of the patient, radiation treatment results data based on the RTP data, the personalized data of the patient, etc., which are required to generate RTP data.

In this case, the RT-IS 140 may collect/store the personalized data of the patient in conjunction with the HIS 130, the CIS 150, etc., and may also store a plurality of preset RTP data.

In this case, the plurality of preset RTP data may be reference RTP data previously modeled in conformity with specific criteria, and the personalized data of the patient may include one or more of age, gender, weight, height, medical history, the occurrence of menopause, diagnosis, an Eastern Cooperative Oncology Group (ECOG)/Karnofsky Performance Status (KPS) index, the occurrence of metastasis, a primary Tumor, regional lymph Node, distant Metastasis (TNM) class, chemical therapy, a region of treatment, a treatment pattern, immunity, sensitivity, and the singularity of past treatment. The KPS index is one of the methods of classifying the whole body activities of the patient, and is an index representing physical status from death to normal body status by a value ranging from 0 to 100[%]. It will be apparent that the KPS index is not necessarily limited to data in which personalized data is described, and may include all information about the characteristics of each individual patient.

Furthermore, the RT-IS 140 may perform the function of the RTP apparatus according to the present invention, which will be described in detail later with reference to FIGS. 2 to 4.

The client device 160, which is a user device for establishing an RTP, may be an RT-PACS, may be provided with the medical images of a patient from at least one of the medical imaging device 110, the PACS 120, and the RT-IS 140, and may be provided with radiation treatment results data based on the RTP data of the patient and the personalized data of the patient from the RT-IS 140. It will be apparent that the client device 160 may also directly store the personalized data of the patient depending on the circumstances.

Furthermore, the client device 160 is a device corresponding to the RTP apparatus of the present invention, and may establish an RTP therein or may establish an RTP in conjunction with the RT-IS 140.

Such an RTP apparatus according to the present invention will be described in detail with reference to FIGS. 2 to 4.

Figure 2:
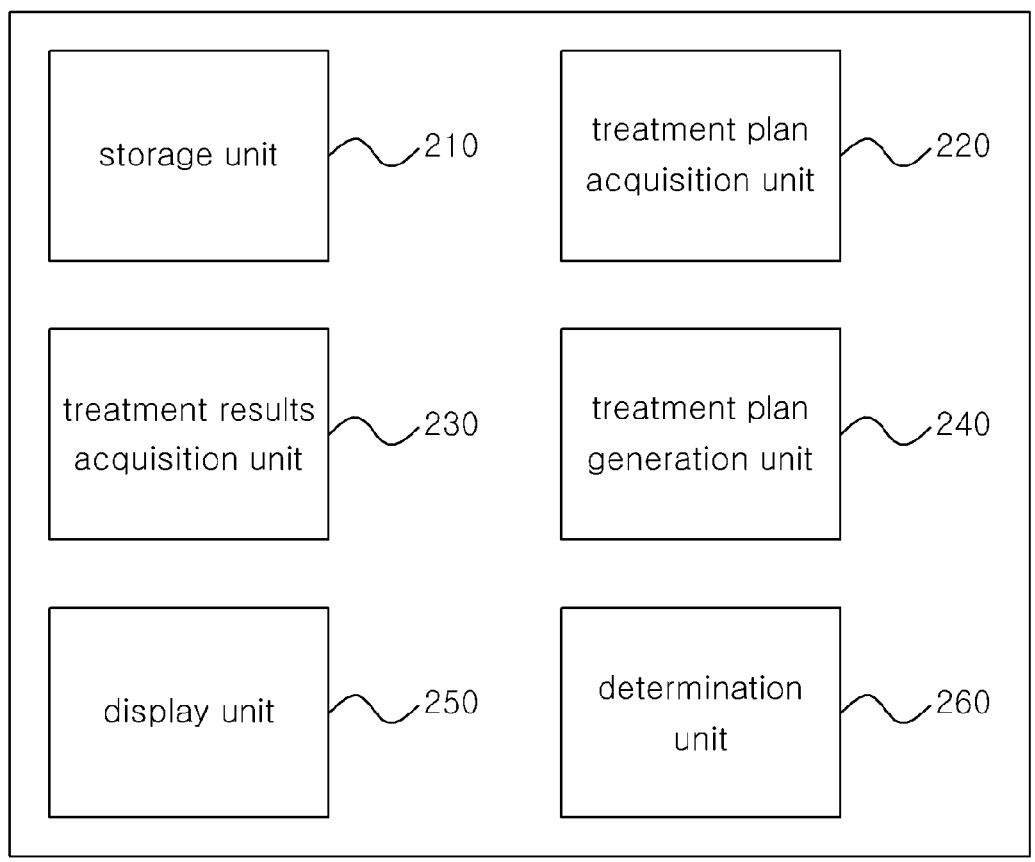
FIG. 2 shows the configuration of an RTP apparatus according to an embodiment of the present invention.

FIG. 2 illustrates the configuration of an RTP apparatus according to an embodiment of the present invention. Although the RTP apparatus may be implemented in the RT-IS 140 or the client device 160, the client device 160 will be described as an example in FIG. 2.

Referring to FIG. 2, the RTP apparatus includes a storage unit 210, a treatment plan acquisition unit 220, treatment results acquisition unit 230, a treatment plan generation unit 240, a display unit 250, and a determination unit 260.

The storage unit 210 may store medical images of patients, a plurality of preset RTP data, that is, modeled reference RTP data, the previous RTP data of the patients, and radiation treatment results data based on the previous RTP data of the patients.

In this case, the personalized data may include one or more of age, gender, weight, height, medical history, the occurrence of menopause, diagnosis, an ECOG/KPS index, the occurrence of metastasis, a TNM class, chemical therapy, a region of treatment, a treatment pattern, immunity, sensitivity, and the singularity of past treatment.

Furthermore, the storage unit 210 may include at least one preset RTP data for the radiation treatment of each patient. In this case, the at least one preset RTP data may be any one of a plurality of modeled reference RTP data or may be RTP data newly generated using the reference RTP data.

The treatment plan acquisition unit 220 acquires RTP data corresponding to the medical image of the patient from among a plurality of preset RTP data based on a medical image of a region of interest of the patient, that is, the radiation treatment region of the patient. It will be apparent that the treatment plan acquisition unit 220 may acquire the corresponding RTP data from among a plurality of preset RTP data additionally using the personalized data of the patient if necessary.

In this case, the treatment plan acquisition unit 220 may extract information about a region of radiation treatment, the size of cancer, etc. from the medical image of the patient, and may acquire RTP data corresponding to the extracted information.

Figure 3:
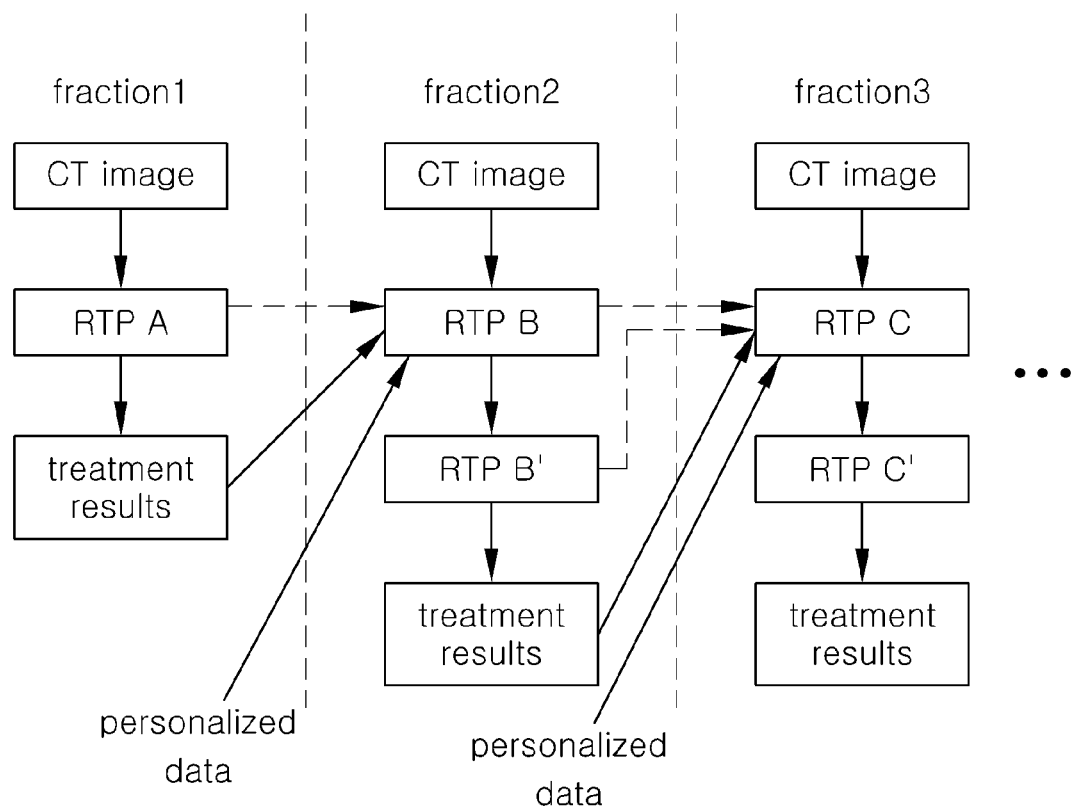
FIG. 3 shows an illustrative diagram illustrating the RTP apparatus shown in FIG. 2.

For example, as in fraction 1 shown in FIG. 3, RTP A corresponding to the CT image of a patient is acquired using the CT image of the patient in fraction 1.

The treatment results acquisition unit 230 acquires radiation treatment results data based on the RTP data acquired by the treatment plan acquisition unit 220.

In this case, the radiation treatment results data may include not only historical information, such as a dose volume histogram (DVH) and radiation doses to a tumor and normal internal organs, but also numerical data, such as the power consumption (monitor unit (MU)) of a radiation treatment apparatus.

The treatment plan generation unit 240 generates subsequent RTP data for a region of interest of the patient using the radiation treatment results data based on previous RTP data and the personalized data of the patient.

In this case, the treatment plan generation unit 240 may generate third RTP data from the preset second RTP data previously set as the subsequent RTP data using the radiation treatment results data based on the previous RTP data and the personalized data of the patient.

It will be apparent that the treatment plan generation unit 240 may generate new RTP data additionally using information about the previous RTP data if necessary.

For example, as illustrated in FIG. 3, to generate RTP B' from RTP data preset in fraction2, that is, RTP B, radiation treatment results data in fraction1 and the personalized data of the patient are used, and, if necessary, RTP A, that is, RTP data in fraction1, may be used.

Furthermore, to generate RTP C' from RTP C, that is, RTP data preset in fraction3, radiation treatment results data in fraction2 and the personalized data of the patient are used. It will be apparent that at least one of RTP B, that is, first RTP data in fraction2, and RTP B', that is, newly generated treatment plan data, may be used if necessary.

Although the new RTP data (RTP B', and RTP C') has been described as being generated from the previously acquired RTP data (RTP B, and RTP C) using CT images in fraction2 and fraction3 of FIG. 3, the present invention is not limited thereto, and new RTP data may be generated using treatment results data in a previous fraction and the personalized data of the patient without using CT images of the patient. That is, in fraction2, RTP B' is generated using the treatment results data in fraction1 and the personalized data of the patient, and in fraction3, RTP C' is generated using the treatment results data in fraction2 and the personalized data of the patient. In this case, RTP data generated in a previous fraction may be additionally used if necessary.

Although RTP A, RTP B, and RTP C illustrated in FIG. 3 have been described as different RTP data, the present invention is not limited thereto, but they may be the same RTP data.

As another embodiment, the treatment plan generation unit 240 may generate RTP data in a corresponding fraction using the purpose of radiation treatment in the corresponding fraction, radiation treatment results data in a previous fraction, and, if necessary, the personalized data of the patient.

In this case, the purpose of treatment may be determined for each fraction, but may be determined for each plan, each including a plurality of fractions. It is preferable to determine the purpose of treatment for each plan.

In this case, the purpose of treatment may include a purpose to completely eliminate a tumor, a purpose to mitigate pain, a purpose to reduce a tumor, a purpose to prevent recurrence, etc., and may be a factor for determining the direction of a subsequent plan by selecting only one from among a plurality of purposes, such as checking whether a patient is male or female.

The display unit 250 displays the RTP data generated by the treatment plan generation unit 240 on a screen, thereby providing newly generated RTP data to the user.

In this case, the display unit 250 may be provided in the client device 160, but may not be provided in the RT-IS 140.

The determination unit 260 may receive user input, that is, input related to whether to use generated RTP data, from the user, and may determine whether to use the generated RTP data as the RTP data of the patient according to the received user input.

In this case, the determination unit 260 may be provided in the client device 160, but may not be provided in the RT-IS 140.

FIGS. 2 and 3 illustrate the generation of RTP data between fractions. An RTP apparatus according to the present invention is not limited to the generation of RTP data between fractions, and may generate new RTP data in a single fraction. This will be described with reference to FIGS. 4 and 5.

Figure 4:
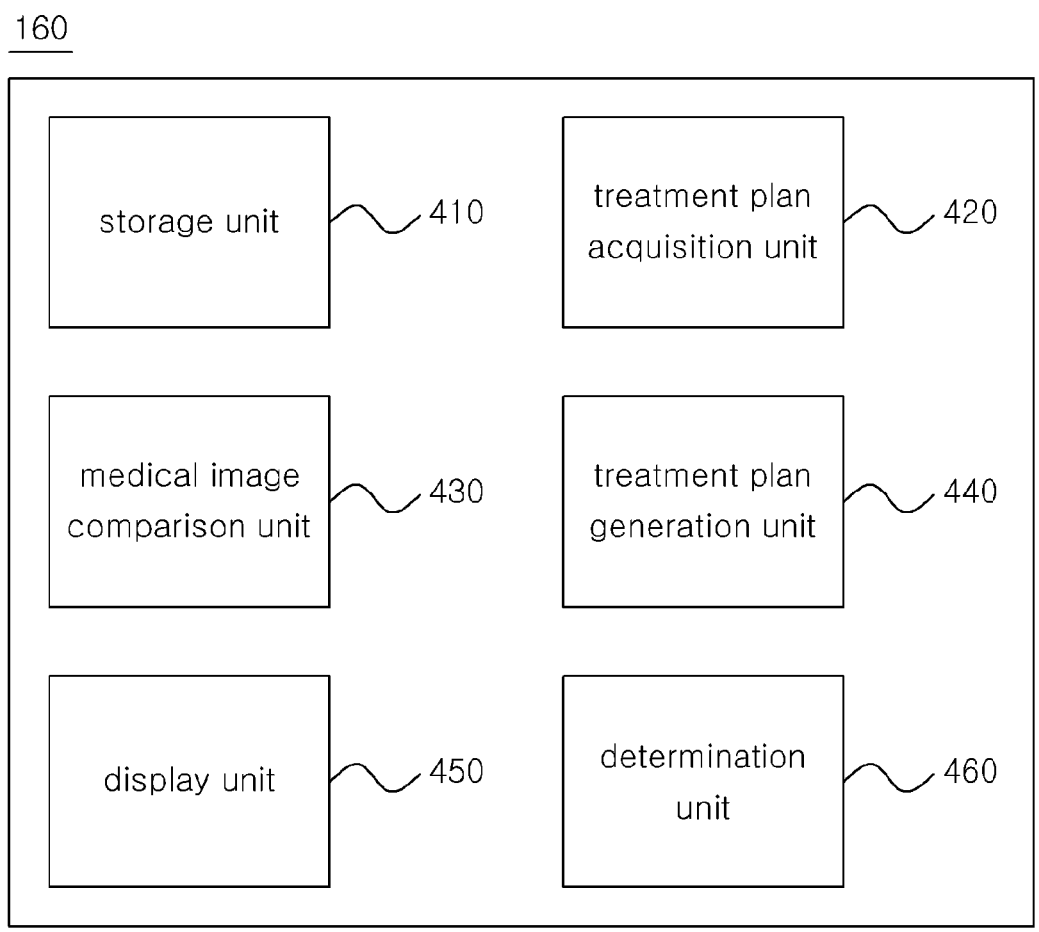
FIG. 4 shows the configuration of an RTP apparatus according to another embodiment of the present invention.

FIG. 4 is a diagram showing the configuration of an RTP apparatus according to another embodiment of the present invention. Although the RTP apparatus may be implemented in an RT-IS or a client device, the client device will be described as an example in FIG. 4.

Referring to FIG. 4, the RTP apparatus includes a storage unit 410, a treatment plan acquisition unit 420, a medical image comparison unit 430, a treatment plan generation unit 440, a display unit 450, and a determination unit 460.

The storage unit 410 may store medical images of the patient, a plurality of preset RTP data, that is, modeled reference RTP data, the previous RTP data of the patient, and radiation treatment results based on the previous RTP data of the patient, and may further include one or more RTP data preset for the radiation treatment of the patient.

In this case, the personalized data may include one or more of age, gender, weight, height, medical history, the occurrence of menopause, diagnosis, an Eastern Cooperative Oncology Group (ECOG)/Karnofsky Performance Status (KPS) index, the occurrence of metastasis, a primary Tumor, regional lymph Node, distant Metastasis (TNM) class, chemical therapy, a region of treatment, a treatment pattern, immunity, sensitivity, and the singularity of past treatment.

In this case, the personalized data may be requested from the RT-IS, received therefrom, and then stored.

The treatment plan acquisition unit 420 acquires RTP data corresponding to medical images of the patient from among a plurality of predetermined RTP data based on a medical image of the region of interest of the patient, that is, the radiation treatment region of the patient. It will be apparent that the treatment plan acquisition unit 420 may acquire the corresponding RTP data from among a plurality of preset RTP data additionally using the personalized data of the patient if necessary.

In this case, the treatment plan acquisition unit 420 may extract information about a region of radiation treatment, the size of cancer, etc. from the medical image of the patient, and may acquire RTP data corresponding to the extracted information.

Figure 5:
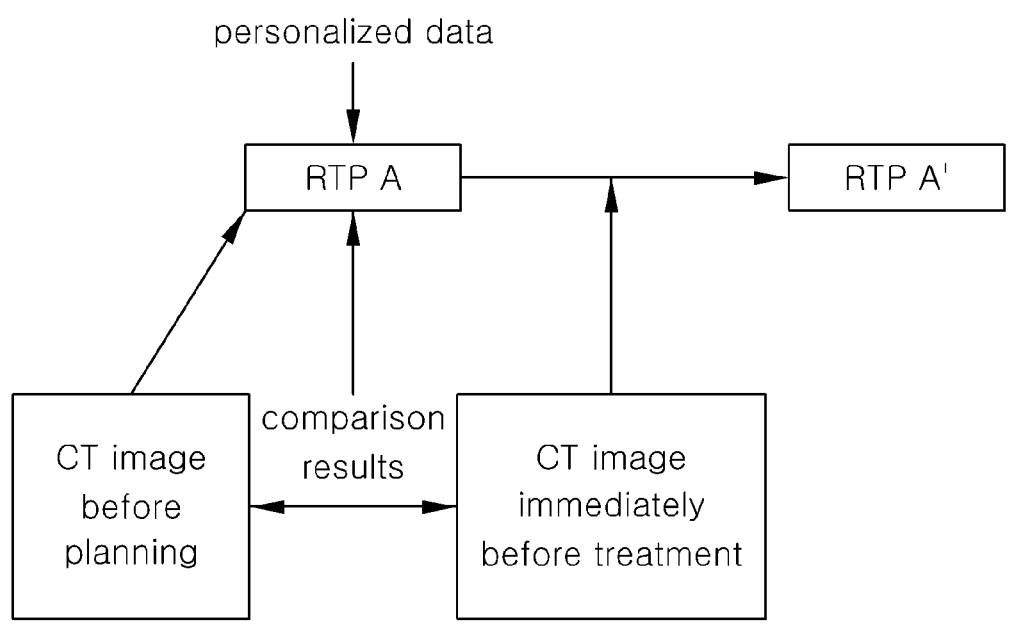
FIG. 5 shows an illustrative diagram illustrating the RTP apparatus shown in FIG. 4.

For example, as shown in FIG. 5, RTP A which is the corresponding RTP data of a plurality of RTP data is acquired using a CT image before planning.

The medical image comparison unit 430 compares a medical image of the patient required to acquire RTP data with a medical image of the patient acquired after the acquisition of the RTP data.

For example, as shown in FIG. 5, a CT image before the planning of the RTP data is compared with a CT image after planning, that is, a CT image immediately before treatment.

The treatment plan generation unit 440 generates new RTP data from previously acquired RTP data based on the results of comparison between a medical image before planning and a medical image immediately before treatment and personalized data.

For example, the treatment plan generation unit 440 generates RTP A', that is, new RTP data, from RTP A acquired via a CT image before planning using the results of comparison between the medical images and the personalized data of the patient.

As another embodiment, the treatment plan generation unit 440 may generate new RTP data from acquired RTP data using the purpose of treatment as well as the results of comparison between the medical images and the personalized data of the patient.

The display unit 450 displays the RTP data generated by the treatment plan generation unit 440 on a screen, thereby providing the generated RTP data to the user.

The determination unit 460 may receive user input, that is, input related to whether to use generated RTP data, from the user, and may determine whether to use the generated RTP data as the RTP data of the patient in accordance with the received user input.

Figure 6:
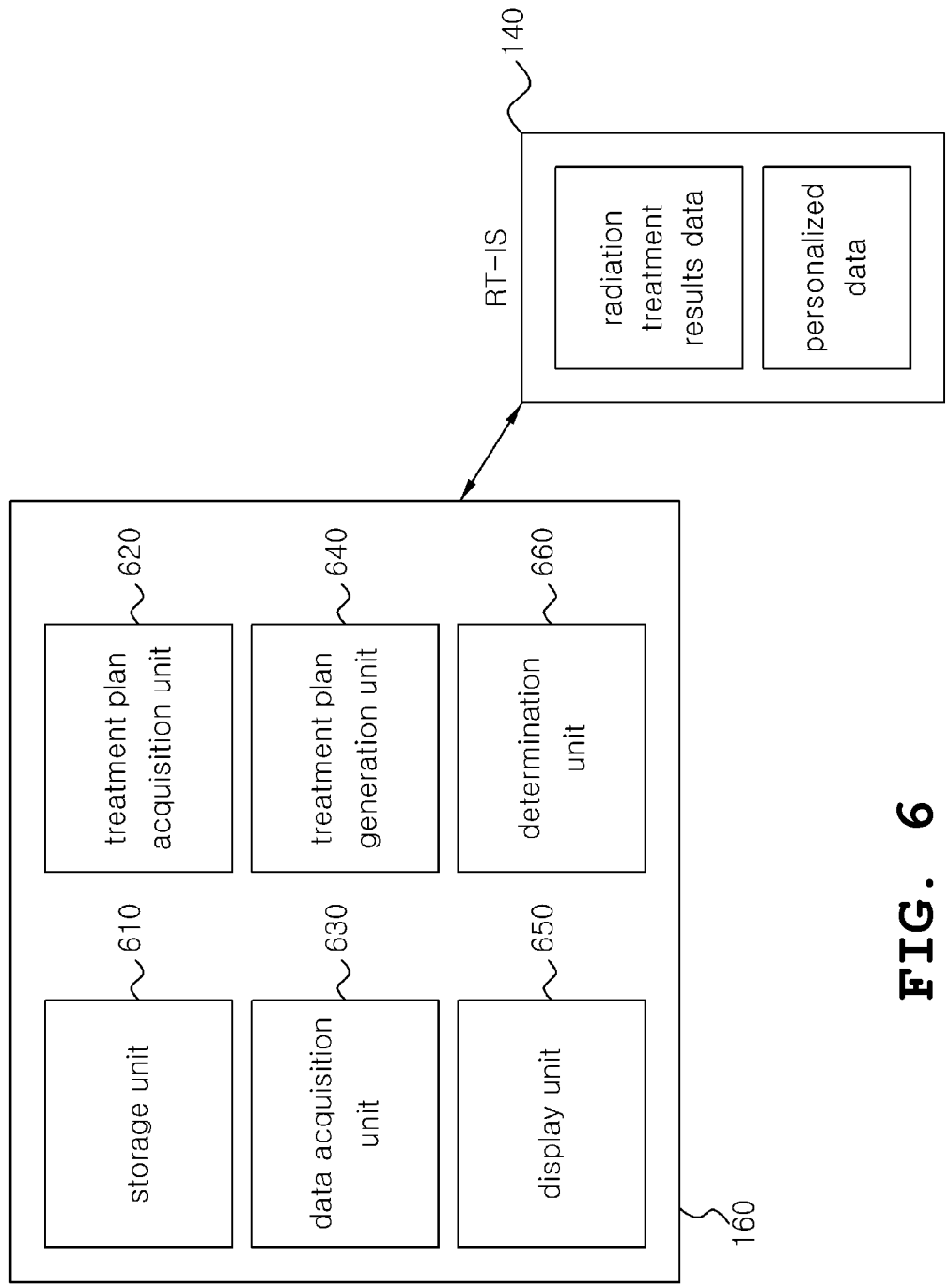
FIG. 6 shows the configuration of an RTP system according to an embodiment of the present invention.

FIG. 6 is a diagram showing the configuration of an RTP system according to an embodiment of the present invention, and illustrates the configuration of a system for generating RTP data using radiation treatment results data.

Referring to FIG. 6, the RTP system includes a client device 160 and an RT-IS 140 shown in FIG. 1.

The RT-IS 140 stores radiation treatment results data based on the previous RTP data of each patient, the personalized data of the patient.

In this case, the RT-IS 140 may store the previous RTP data of the patient, RTP data generated from the previous RTP data, and a medical image of the region of interest of the patient depending on circumstances.

The client device 160 includes a storage unit 610, a treatment plan acquisition unit 620, a data acquisition unit 630, a treatment plan generation unit 640, a display unit 650, and a determination unit 660.

The storage unit 610 stores a plurality of RTP data previously modeled, and, if necessary, medical images of a patient.

It will be apparent that the storage unit 610 may store not only the above-described data, but also relevant data required to establish an RTP in the client device of the present invention.

The treatment plan acquisition unit 620 acquires RTP data corresponding to a medical image of the patient from among a plurality of RTP data stored in the storage unit 610 based on a medical image before planning for the region of interest of the patient, that is, the radiation treatment region of the patient. It will be apparent that the treatment plan acquisition unit 620 may acquire corresponding RTP data additionally using the personalized data of the patient received from the RT-IS 140 if necessary.

The data acquisition unit 630 requests and receives radiation treatment results data based on the RTP data, acquired from the medical image of the patient before planning, and the personalized data of the patient from the RT-IS 140.

The treatment plan generation unit 640 generates RTP data in a subsequent fraction for the region of interest of the patient using radiation treatment results data based on RTP data in a previous fraction and the personalized data of the patient received from the RT-IS 140.

The display unit 650 displays the RTP data generated by the treatment plan generation unit 640 on a screen, thereby providing the generated RTP data to the user.

The determination unit 660 may receive user input, that is, input related to whether to use generated RTP data, from the user, and may determine whether to use the generated RTP data as the RTP data of the patient in accordance with the received user input.

In this manner, the RTP apparatus and system according to the present invention establish new RTP data using radiation treatment results data in a previous fraction and the personalized data of the patient, thereby reducing the time and cost that are required to establish an RTP.

Furthermore, the present invention may generate new RTP data by additionally taking into account the purpose of radiation treatment, and may modify the preset RTP data of the patient via the comparison between a medical image before planning and a medical image immediately before treatment in a single fraction, thereby omitting an existing procedure for establishing an RTP and accordingly reducing the time and cost that are required to generate RTP data.

FIG. 7 is an operation flowchart showing an RTP method according to an embodiment of the present invention, and illustrates the process of establishing RTP data using radiation treatment results data and personalized data.

Referring to FIG. 7, the RTP method stores a plurality of previously modeled RTP data at step S710.

In this case, the plurality of RTP data may be RTP data modeled by taking into account the purposes of treatment, ages, the regions of treatment, etc., and may be modeled using the RTP data of many patients.

Once a medical image of a region of interest corresponding to the region of treatment of the patient has been acquired, first RTP data, belonging to the plurality of RTP data and corresponding to medical image of the patient, is acquired using the acquired medical image of the patient at steps S720 and S730.

In this case, at step S720, the first RTP data may be acquired using the personalized data of the patient in addition to the medical image of the patient.

Once radiation treatment based on the acquired first RTP data has been performed and corresponding radiation treatment results data has been acquired, third RTP data is generated from preset second RTP data using the acquired radiation treatment results data and the personalized data of the patient at steps S740 and S750.

In this case, the first RTP data may be RTP data in a first fraction set for the radiation treatment of the patient, and the second RTP data may be preset RTP data in a second fraction, in which case the second RTP data may be the same as the first RTP data.

Once the new third RTP data has been generated, the generated third RTP data is provided to a user, that is, a radiation treatment specialist, and it is determined in accordance with the decision of the user whether the generated third RTP data will be used as the RTP data of the patient at steps S760 to S780.

In this case, if it is determined at step S770 that the user will not use the generated third RTP data, the process of generating new RTP data again using the preset second RTP data or by taking into account the additional input of the user may be repeated.

Although the radiation treatment results data has been described as being used In FIG. 7, the RTP method according to the present invention is not limited thereto, but new RTP data may be generated additionally using the purpose of radiation treatment, as described above in connection with the apparatus.

Furthermore, although the third RTP data has been described as being generated from the preset second RTP data at step S750, the present invention is not limited thereto, but third RTP data may be generated using the acquired radiation treatment results data and the personalized data of the patient.

FIG. 8 is an operation flowchart showing an RTP method according to another embodiment of the present invention, and illustrates the process of establishing RTP data via the comparison between two medical images in a single fraction.

Referring to FIG. 8, the RTP method stores a plurality of previously modeled RTP data at step S810.

In this case, the plurality of RTP data may be RTP data modeled by taking into account the purposes of treatment, ages, the regions of treatment, etc., and may be modeled using the RTP data of many patients.

Once a medical image of a region of interest corresponding to the region of treatment of the patient has been acquired, first RTP data, belonging to the plurality of RTP data and corresponding to medical image of the patient, is acquired using the acquired medical image of the patient at steps S820 and S830.

In this case, at step S820, the first RTP data may be acquired using the personalized data of the patient in addition to the medical image of the patient.

Once a second medical image of the region of interest of the patient has been acquired after the acquisition of the first RTP data, the two acquired medical images, that is, the first medical image and the second medical image, are compared with each other at steps S840 and S850.

Second RTP data is generated from the first RTP data acquired at step S830 using the results of the comparison at step S850, that is, the results of the comparison between the two medical images and the personalized data of the patient at steps S840 and S850.

Once the new second RTP data has been generated, the generated second RTP data is provided to a radiation treatment specialist and it is determined in accordance with the decision of the user whether the generated second RTP data will be used as the RTP data of the patient at steps S860 to S880.

In this case, if it is determined at step S870 that the user will not use the generated second RTP data, the process of generating new RTP data again using the preset first RTP data or by taking into account the additional input of the user may be repeated.

Although the difference between medical images and the personalized data have been described as being used in FIG. 8, as in FIG. 7, the RTP method according to the present invention is not limited thereto, but new RTP data may be generated additionally using the purpose of radiation treatment.

The radiation treatment planning method according to the embodiment of the present invention may be implemented in the form of program instructions that can be executed via various computer means, and may be stored in a computer-readable medium. The computer-readable medium may include one of program instructions, data files, and data structures, or program instructions, data files, and data structures in combination. The program instructions recorded in the computer-readable medium may be program instructions that are specially designed and configured for the present invention or that are well known to and can be used by those having ordinary knowledge in the field of computer software. Examples of the computer-readable medium includes magnetic media such as a hard disk, a floppy disk and magnetic tape, optical media such as CD-ROM and a DVD, magneto-optical media such as a floptical disk, and hardware devices that are specially configured to store and execute program instructions, such as ROM, RAM, and flash memory. The examples of the program instructions include not only machine language code that is generated by a compiler, but also high-level language that can be executed by a computer. The above-described hardware apparatus may be configured to operate as one or more software modules in order to perform the operation of the present invention, and vice versa.

According to the present invention, a new RTP of a patient can be generated using the previous radiation treatment results data (including historical information such as a dose volume histogram (DVH), doses, etc.) of a patient and, if necessary, the previous RTP data of the patient, thereby reducing the time and cost that are required to establish the RTP.

In detail, the present invention can generate subsequent RTP data by considering radiation treatment results based on the previously acquired RTP data of a patient and the personalized data of the patient (including personal information about the patient, medical history of the patient, etc.), thereby reducing the time required to generate RTP data and effectively establishing subsequent RTP data in accordance with the personal characteristics of the patient.

Furthermore, the present invention can generate new RTP data by additionally considering the purpose of radiation treatment, and thus a medical imaging procedure and an existing RTP establishment procedure can be omitted, thereby reducing the time and cost that are required to generate RTP data.

Furthermore, the present invention can correct (modify) RTP data acquired via a first medical image while considering the difference between the first medical image of a patient used to acquire RTP data, a second medical image of the patient acquired immediately before treatment, and the personalized data of the patient, thereby reducing the time and cost that are required to establish new RTP data.

Although the present invention has been described with reference to the definite items, such as specific components, and the limited embodiments and drawings, the above description is intended merely to help the overall understanding of the present invention, but the present invention is not limited to the above embodiments. From the above description, it will be apparent to those having ordinary knowledge in the technical field to which the present invention pertains that various modifications and variations are possible.

Accordingly, the spirit of the present invention should not be determined only based on the above-described embodiments, and the accompanying claims and equal or equivalent modifications thereof are consider to fall within the scope of the spirit of the present invention.

What is claimed is:

1. A radiation treatment planning apparatus, comprising:
a processor configured to:
    acquire first radiation therapy plan (RTP) data generated based on a first medical image of a region of interest of a patient;
    acquire first radiation therapy results data for the region of interest resulting from a first radiation therapy based on the first RTP data;
    acquire preset second RTP data generated based on a second medical image of the region of interest of the patient acquired after the first radiation therapy is performed;
    acquire second radiation therapy results data for the region of interest resulting from a second radiation therapy based on the second RTP data; and
    generate third RTP data based on the first RTP data and the second RTP data for the region of interest using the second radiation therapy results data and personalized data of the patient.

2. The radiation treatment planning apparatus of claim 1, wherein the personalized data includes at least one of age, gender, weight, height, medical history, occurrence of menopause, diagnosis, an Eastern Cooperative Oncology Group (ECOG)/Karnofsky Performance Status (KPS) index, regional lymph Node, distant Metastasis (TNM) class, chemical therapy, a region of treatment, a treatment pattern, immunity, sensitivity, and singularity of past treatment.

3. The radiation treatment planning apparatus of claim 1, wherein the processor is further configured to:

generate the third RTP data from the second RTP data using the second radiation therapy results data and a predetermined purpose of treatment of the second RTP data.

4. The radiation treatment planning apparatus of claim 1, wherein the processor is further configured to:

acquire the first RTP data from among a plurality of preset RTP data based on at least one of the medical image and the personalized data of the patient.

5. The radiation treatment planning apparatus of claim 1, the processor is further configured to:

provide the third RTP data to a user, and determine whether to use the third RTP data as RTP data of the patient in accordance with input of the user.

6. A radiation treatment planning method, comprising:

acquiring, by a processor, first RTP data generated based on a first medical image of a region of interest of a patient;

acquiring, by the processor, first radiation therapy results data for the region of interest resulting from a first radiation therapy based on the first RTP data;

acquiring, by the processor, preset second RTP data generated based on a second medical image of the region of the interest of the patient acquired after the first radiation therapy is performed;

acquiring, by the processor, second radiation therapy results data for the region of interest resulting from a second radiation therapy based on the second RTP data; and generating, by the processor, third RTP data based on the first RTP data and the second RTP data for the region of interest using the second radiation therapy results data and personalized data of the patient.

7. The radiation treatment planning method of claim 6, wherein the generating is configured to generate the third RTP data from the second RTP data using the second radiation therapy results data and a predetermined purpose of treatment of the second RTP data.

8. The radiation treatment planning method of claim 6, further comprising:

providing, by the processor, the third RTP data to a user; and determining, by the processor, whether to use the third RTP data as RTP data of the patient in accordance with input of the user.

* * * * *